United States Patent [19]

Smith et al.

[11] Patent Number: 5,236,609
[45] Date of Patent: Aug. 17, 1993

[54] STERILIZABLE LUBRICANT

[75] Inventors: Rory J. M. Smith, Hebden; David R. J. Green, Camberley, both of England

[73] Assignee: Chas F Thackray Limited, England

[21] Appl. No.: 645,058

[22] Filed: Jan. 24, 1991

[51] Int. Cl.$^5$ ............................................. C10M 173/02
[52] U.S. Cl. .................... 252/49.3; 252/52 R; 252/56 R
[58] Field of Search ................ 252/49.3, 52 R, 56 R

[56] References Cited

U.S. PATENT DOCUMENTS

| | | | |
|---|---|---|---|
| 3,852,032 | 12/1974 | Urbach | 21/541 R |
| 4,378,299 | 3/1983 | Alexander | 252/49.3 |
| 4,461,712 | 7/1984 | Jonnes | 252/49.3 |
| 4,659,700 | 4/1987 | Jackson | 514/55 |
| 4,781,847 | 11/1988 | Weitz | 252/49.3 |

FOREIGN PATENT DOCUMENTS

| | | |
|---|---|---|
| 2546066 | 11/1964 | France. |
| WO88/03414 | 11/1988 | PCT Int'l Appl.. |
| 1203611 | 8/1970 | United Kingdom. |
| 2029848 | 3/1980 | United Kingdom. |

Primary Examiner—Ellen McAvoy
Attorney, Agent, or Firm—Barnes & Thornburg

[57] ABSTRACT

A lubricant gel formulation for surgical and external applications is described. The gel comprises an acrylic acid polymer, a hydroxy compound having at least two hydroxy groups and water. The gel composition exhibits exceptional viscosity stability through two cycles of gamma radiation sterilization. The gel formulation can be manufactured and packaged in sealed containers and radiation sterilized without significant decrease in rheological properties.

21 Claims, No Drawings

STERILIZABLE LUBRICANT

This invention relates to gel of the kind having surgical and external uses as a lubricant, emolient or both.

Sterilisation of lubricant gels for surgical applications has presented problems. Thermal sterilisation can cause tubes or other containers to burst unless air ballasted autoclaves are employed. Glycosidic links of conventional cellulosic gels are cleaved by gamma radiation. The viscosity of the gel is reduced, destroying the lubricity characteristic.

According to a first aspect of the present invention, a lubricant gel includes an acrylic acid polymer, a hydroxy compound having two or more hydroxy groups and water.

Other compounds may be present.

The acrylic acid polymer may be a homopolymer or copolymer of acrylic acid or a derivative thereof. Acrylic acid polymers cross-linked with allylsucrose, known as carbomers are preferred. Carbomers, discussed in Martindale (The Extra Pharmacopoeia) 27th ed. Pharmaceutical Press p919, are powders which dissolve in water to give acidic solutions. Neutralisation of the solutions may be necessary to form a gel. Preferred carbomers are manufactured under the Trade Mark CARBOPOL (BF Goodrich). Preferred acrylic acid polymers have molecular weights of 1 million or greater, preferably 2 million or greater but also preferably less than 4 million. Preferred acrylic acid polymers afford aqueous solutions having a visosity of 50–150,000 cps at 1% concentration. Use of CARBOPOL 934,940 or 954 is particularly preferred.

The hydroxy compound having two or more hydroxl groups may comprise a diol, triol or polyol. Presence of 1,2-diol groupings is preferred. Hydroxy compounds, having 2-4 carbon atoms have been found to be Particularly useful. Glycerol is especially preferred. Other preferred compounds include ethane-1,2-diol; propane-1,2-diol, butane-1,3-diol and butane-1,4-diol. Mixtures of hydroxy compounds may be employed, especially mixtures of glycerol and one or more diols. A base, for example, sodium hydroxide, may be provided in an amount to neutralise the acrylic acid polymer.

Gels in accordance with this invention have been found to be sterilisable by gamma radiation without a significant decrease in rheological properties. The need for autoclaving is avoided. The gels are preferably thixotropic, facilitating adhesion to surfaces after application.

The proportion of hydroxy compound or compounds in the gel preferably lies in the range from a trace to 15%. Percentages referred to in the specification are by weight unless indicated otherwise. Preferred gels include 4–8% of hydroxy compound, particularly approximately 5%.

Corrosion inhibitors may be included in the gels. These are preferably radiation stable. Use of sodium nitrite is preferred. Use of a corrosion inhibitor is useful in preventing corrosion of surgical instruments or other apparatus. Such gels may be intended for external use only, dependent on the nature or the inhibitor.

An anaesthetic, for example lignocaine, may be incorporated in the gel. A preservative may be used to prevent bacterial spoilage of the gel. NIPAGIN M or NIPOLSOL M (Nipa Laboratories) have been found to be efficacious.

Conductive salts, for example potassium chloride, potassium nitrate, potassium nitrite, sodium chloride, sodium nitrate and sodium nitrite may be included to facilitate use as an electrode gel or ultrasound gel.

Sequestering agents may be employed to protect the gel from the destructive effects of polyvalent cations. Any suitable sequestering agent may be used, for example: disodium hydroxy ethane-1,1-diphosphonate (HYQUEST 20, S G Stead). Polyvalent ions may be leached in use from the surfaces of the instruments or other materials.

According to a second aspect of the present invention, the method of forming a sterile lubricant comprises the steps of: providing a gel in accordance with the first aspect of this invention, placing a quantity of said gel in a sealed container and exposing the gel to a sterilising intensity of ionising radiation.

The container may comprise any conventional container for dispensing surgical gels, including metal or plastics, bottles, jars or tubes. Metal containers may be lacquered internally to prevent corrosion on storage.

According to a third aspect of the present invention, we provide use of a gel as previously disclosed for manufacture of a radiation sterilisable lubricating gel.

The invention is further described by means of the following examples which are not limitative.

EXAMPLES 1 AND 2

Gels were prepared as described in Table 1, sodium hydroxide being added to neutralise the polymer.

TABLE 1

|  | Comp 1 | Comp 2 | Ex. 1 | Comp 3 | Ex. 2 |
| --- | --- | --- | --- | --- | --- |
| Carbopol 934P | 0.75 | 1.0 | 0.75 | — | — |
| Carbopol 954 | — | — | — | 1.0 | 1.0 |
| Carbopol 951 | 0.75 | 0.75 | — | 0.75 | — |
| Glycerol | — | — | 5.0 | — | 5.0 |
| Water to balance |  |  |  |  |  |
| Viscosity before irradiation ($10^3$ cps) | 103 | 146 | 132 | 125 | 142 |
| Viscosity after irradiation ($10^3$ cps) | 0.2 | 1.7 | 108 | 0.1 | 88.1 |

Viscosities were measured before and after gamma irradiation at a dosage of 2.9 m Rads.

EXAMPLE 3

A gel was compounded with the following ingredients. The ingredients, excluding CARBOPOL were mixed in the aqueous phase. CARBOPOL was added under high shear and the mixture was allowed to stand for one minute. Aqueous sodium hydroxide was added to bring the PH to 6.5.

| Carbopol 934P | 0.75% |
| --- | --- |
| Glycerol | 5.00% |
| Nipagen M Sodium | 0.03% |
| Hiquest 20 | 100 ppm |
| Water to balance | 100% |

Viscosities before and after irradiation were 112,000 and 103,000 cps respectively.

The composition of Example 3 exhibited excellent retention of viscosity upon storage after one or two cycles of radiation sterilization. Results are set out in Tables 2, 3 and 4. The product was thawed in a laquered metallic tube, the preservatives Nipagen and Nipasol were added in the proportions shown.

TABLE 2

| TIME | CONTROL | 1 RADIATION CYCLE | 10° C. 2 RADIATION CYCLES |
|---|---|---|---|
| INITIAL | pH 6.33 | pH 6.20 | pH 6.19 |
|  | 121.280 cps | 97.680 cps | 100.720 cps |
|  | 0.140% Nipagin | 0.131% Nipagin | 0.132% Nipagin |
|  | 0.029% Nipasol | 0.037% Nipasol | 0.028% Nipasol |
| 1 MONTH | pH 6.26 | pH 6.27 | pH 6.35 |
|  | 115.680 cps | 99.520 cps | 94.720 cps |
|  | 0.147% Nipagin | 0.148% Nipagin | 0.143% Nipagen |
|  | 0.025% Nipasol | 0.038% Nipasol | 0.028% Nipasol |
| 3 MONTHS | pH 6.52 | pH 6.55 | pH 6.61 |
|  | 120.560 cps | 96.560 cps | 98.360 cps |
|  | 0.142% Nipagin | 0.146% Nipagin | 0.148% Nipagin |
|  | 0.022% Nipasol | 0.042% Nipasol | 0.031% Nipasol |

TABLE 3

| TIME | CONTROL | 1 RADIATION CYCLE | Room Temperature 2 RADIATION CYCLES |
|---|---|---|---|
| INITIAL | pH 6.33 | pH 6.20 | pH 6.19 |
|  | 121.280 cps | 97.680 cps | 100.720 cps |
|  | 0.140% Nipagin | 0.131% Nipagin | 0.132% Nipagin |
|  | 0.029% Nipasol | 0.037% Nipasol | 0.028% Nipasol |
| 1 MONTH | pH 6.33 | pH 6.35 | pH 6.33 |
|  | 116.560 cps | 97.520 cps | 95,200 cps |
|  | 0.162% Nipagin | 0.142% Nipagin | 0.143% Nipagin |
|  | 0.025% Nipasol | 0.020% Nipasol | 0.051% Nipasol |
| 3 MONTHS | pH 6.45 | pH 6.48 | pH 6.60 |
|  | 121.680 cps | 96.560 cps | 93.760 cps |
|  | 0.159% Nipagin | 0.150% Nipagin | 0.148% Nipagin |
|  | 0.050% Nipasol | 0.035% Nipasol | 0.031% Nipasol |
| 6 MONTHS | pH 6.52 | Not Available | pH 6.45 |
|  | 106.320 cps |  | 76.560 cps |
|  | 0.148% Nipagin |  | 0.130% Nipagin |
|  | 0.026% Nipasol |  | 0.023% Nipasol |

TABLE 4

| TIME | CONTROL | 1 RADIATION CYCLE | 37° C. 2 RADIATION CYCLES |
|---|---|---|---|
| INITIAL | pH 6.33 | pH 6.20 | pH 6.19 |
|  | 121.280 cps | 97.680 cps | 100.720 cps |
|  | 0.140% Nipagin | 0.131% Nipagin | 0.132% Nipagin |
|  | 0.029% Nipasol | 0.037% Nipasol | 0.028% Nipasol |
| 1 MONTH | pH 6.29 | pH 6.36 | pH 6.38 |
|  | 109.120 cps | 98.240 cps | 96.800 cps |
|  | 0.140% Nipagin | 0.143% Nipagin | 0.145% Nipagin |
|  | 0.032% Nipasol | 0.032% Nipasol | 0.031% Nipasol |
| 3 MONTHS | pH 6.56 | pH 6.44 | pH 6.47 |
|  | 102.720 cps | 92.640 cps | 86.720 cps |
|  | 0.154% Nipagin | 0.147% Nipagin | 0.148% Nipagin |
|  | 0.035% Nipasol | 0.015% Nipasol | 0.036% Nipasol |
| 6 MONTHS | pH 6.51 | Not Available | pH 6.44 |
|  | 90.400 cps |  | 69.920 cps |
|  | 0.144% Nipagin |  | 0.131% Nipagin |
|  | 0.026% Nipasol |  | 0.022% Nipasol |

What is claimed is:

1. A lubricant gel consisting essentially of an acrylic acid polymer, at least one hydroxy compound having two or more hydroxy groups, and water.

2. The gel of claim 1 wherein the polymer is a carbomer.

3. The gel of claim 1 wherein the polymer has a molecular weight of 1,000,000 or greater.

4. The gel of claim 1 wherein the polymer has a molecular weight of 2,000,000 or greater.

5. The gel of claim 1 containing acrylic acid polymer at 1% concentration.

6. The gel of claim 1 wherein the hydroxy compound is a 1,2-diol.

7. The gel of claim 1 wherein the hydroxy compound has 2 to 4 carbon atoms.

8. The gel of claim 6 wherein the hydroxy compound is selected from the group consisting of glycerol, ethane-1,2-diol; propane-1,2-diol, butane-1,3-diol and butane-1,4-diol.

9. The gel of claim 7 wherein the hydroxy compound is selected from the group consisting of glycerol, ethane-1,2-diol; propane-1,2-diol, butane-1,3-diol and butane-1,4-diol.

10. The gel of claim 1 wherein two or more hydroxy compounds are included.

11. The gel of claim 10 wherein one of the hydroxy compounds is glycerol.

12. The gel of claim 1 including up to 15% of hydroxy compound.

13. The gel of claim 12 including 4–8% of hydroxy compound.

14. The gel of claim 13 including 5% of hydroxy compound.

15. A method of forming a sterile lubricant comprising the steps of: providing a gel comprising an acrylic acid polymer, a hydroxy compound having two or more hydroxy groups, and water; placing a quantity of said gel in a sealed container and exposing the gel to a sterilising intensity of ionising radiation.

16. A sterile lubricant prepared in accordance with the method of claim 15.

17. A lubricant gel consisting essentially of an acrylic acid polymer, at least one hydroxy compound having two or more hydroxy groups, water, and at least one additional ingredient selected from the group consisting from a corrosion inhibitor, an anaesthetic, a preservative, a conductive salt and a sequestering agent.

18. The gel of claim 17 wherein one additional ingredient is sodium nitrite.

19. The gel of claim 17 wherein one additional ingredient is an anaesthetic.

20. The gel of claim 17 wherein one additional ingredient is a conductive salt.

21. A lubricant gel comprising a carbomer, a hydroxy compound having two or more hydroxy groups, and water.

* * * * *